(12) United States Patent
Sanders et al.

(10) Patent No.: US 10,441,276 B2
(45) Date of Patent: Oct. 15, 2019

(54) SURGICAL SUTURE PASSER AND METHOD OF APPLICATION

(71) Applicant: TENSOR SURGICAL, INC., Chattanooga, TN (US)

(72) Inventors: Brett Sanders, Signal Mountain, TN (US); Keith J. Harper, Chattanooga, TN (US)

(73) Assignee: Tensor, Surgical, Inc, Chattanooga, TN (US)

( * ) Notice: Subject to any disclaimer, the term of this patent is extended or adjusted under 35 U.S.C. 154(b) by 343 days.

(21) Appl. No.: 14/781,079

(22) PCT Filed: Mar. 28, 2014

(86) PCT No.: PCT/US2014/032118
§ 371 (c)(1),
(2) Date: Sep. 29, 2015

(87) PCT Pub. No.: WO2014/189616
PCT Pub. Date: Nov. 27, 2014

(65) Prior Publication Data
US 2016/0296229 A1    Oct. 13, 2016

Related U.S. Application Data

(60) Provisional application No. 61/809,911, filed on Apr. 9, 2013.

(51) Int. Cl.
*A61B 17/06* (2006.01)
*A61B 17/062* (2006.01)
(Continued)

(52) U.S. Cl.
CPC .... *A61B 17/06109* (2013.01); *A61B 17/0482* (2013.01); *A61B 17/062* (2013.01);
(Continued)

(58) Field of Classification Search
CPC . A61B 17/04; A61B 17/0469; A61B 17/0482; A61B 17/0483; A61B 17/06066; A61B 17/06109; A61B 2017/06071–2017/0608; A61B 2017/00805; A61B 2017/0498; A61B 2017/0046; A61B 2017/0482;
(Continued)

(56) References Cited

U.S. PATENT DOCUMENTS 4,596,249 A * 6/1986 Freda ................. A61B 17/0469
606/145
5,562,683 A * 10/1996 Chan ................. A61B 17/0469
289/17
(Continued)

*Primary Examiner* — Jonathan A Hollm
(74) *Attorney, Agent, or Firm* — Carothers & Carothers

(57) ABSTRACT

A surgical suture passer (10) having a hollow needle (11) with an axial lumen (12) and a handle (13) having the hollow needle (11) secured and retained at its proximal end (15). The handle (13) defines a planar recessed surface (21) and the lumen (12) of the hollow needle (11) is aligned with this planar recessed surface (21) when the needle is retained by the handle (13) whereby a suture positioned on the planar surface (21) may be advanced or retracted by direct finger engagement of the suture into and out of the hollow needle lumen (12).

14 Claims, 6 Drawing Sheets

(51) Int. Cl.
*A61B 17/04* (2006.01)
*A61B 17/00* (2006.01)

(52) U.S. Cl.
CPC ............. *A61B 2017/0046* (2013.01); *A61B 2017/00946* (2013.01); *A61B 2017/06052* (2013.01)

(58) Field of Classification Search
CPC ............................. A61B 2017/0052; A61B 2017/06095–2017/061; A61B 5/202; A61B 2018/00523
See application file for complete search history.

(56) References Cited

U.S. PATENT DOCUMENTS

| | | | | |
|---|---|---|---|---|
| 5,993,470 | A | * | 11/1999 | Yoon .................. A61B 17/3496 604/165.02 |
| 5,997,485 | A | * | 12/1999 | Ahmadzadeh ..... A61B 17/3403 600/567 |
| 2011/0301622 | A1 | * | 12/2011 | Oren .................. A61B 17/0483 606/145 |

* cited by examiner

SURGICAL SUTURE PASSER AND METHOD OF APPLICATION

CROSS REFERENCE

This patent applications claims the benefit of U.S. Provisional Patent Application No. 61/809,911, filed on 9 Apr. 2013, for SUTURE PASSER, the entire contents of which are hereby incorporated by reference.

BACKGROUND OF THE INVENTION

The present invention relates to surgical instruments, and pertains particularly to an apparatus and method for passing suture through tissue.

Open surgery is now seldom used where other techniques such as arthroscopic, endoscopic or laproscopic surgical techniques are available because of the benefits to the patient. In open surgical procedures, the suture is typically attached to a needle and the needle is then used to draw the suture through the tissue. However, in closed surgical procedures where an interior surgical site is accessed through a narrow cannula it can be difficult to advance a needle and in particular a curved needle to the interior surgical site.

Therefore in closed surgical procedures, it is common to use a suture passer to pass sutures arthroscopically or percutaneously through tissue at a remote surgical site. Generally the surgical suture passers of the prior art incorporate a handle with a hollow needle extending from the distal end of the handle wherein the suture is advanced through the lumen of the hollow needle. However, such suture passers of the prior art tend to suffer from one or more deficiencies, including but not limited to: size, the need and ability to quickly change suture needles, the inability to reuse and sterilize the handle, complexity of operation, cost of manufacture, etc.

It is a principal object of the present invention to provide a new and improved method and apparatus for passing suture through tissue, such as labial tissue, which does not suffer from one or more of the disadvantages associated with the prior art.

SUMMARY OF THE INVENTION

The surgical suture passer of the present invention includes a hollow needle having an axial lumen and a handle having a proximal end and a distal end, wherein the distal end is adapted to receive and retain the hollow needle. The handle further defines a planar recessed surface wherein the lumen of the needle is aligned with this planar surface when the needle is retained by the handle whereby a suture positioned on this planar surface may be advanced or retracted by direct finger contact and engagement of the suture into and out of the needle lumen. A clamp is provided in the handle and is positioned and manipulatable by a single finger of the operator for easily and quickly clamping and unclamping the hollow needle to the handle against axial movement, whereby needles can be quickly and easily exchanged or the handle may be quickly removed from the needle, leaving the needle in position. This feature also permits the handle to be sterilized and reused.

The clamp in a preferable embodiment consists of a pivotal arm having a notch dimensioned for engaging and binding the hollow needle in position.

The hollow needle is also preferably malleable whereby it may be bent to a desired curvature by the surgeon by hand or with the use of pliers in order to accommodate the surgical site. The recessed planar surface on the handle may further include an outwardly protruding hump for enhancing the finger engagement and advancement or retraction of suture which is positioned on the hump for advancement into or retraction out of the hollow needle lumen. This hump may, if desired, be provided in the form of a roller which may be readily rotated by the surgeons thumb.

The handle may also be provided with a suture passageway slot in the proximal end portion of the handle wherein the slot extends rearwardly toward the proximal end of the handle from the recessed planar surface substantially in alignment with the hollow needle for receiving suture therein for feed and temporary retention. Thus the handle slot may be top loaded with the suture, and in order to prevent the suture from falling out of the slot a spring clip may be provided in the slot which permits the suture to be forced downwardly into the slot past the spring clip for retention thereunder in the slot.

Depending upon the surgical procedure desired or selected, the suture passer may further include a rigid cannulated support shaft which is secured to and protrudes from the distal end of the handle and receives the hollow needle therethrough for support with an outer exposed portion of the needle keyed against rotation to the outer end of the support shaft.

The present invention provides a method for passing suture through an object such as labial tissue wherein a suture passer is provided having a handle with a malleable metal hollow needle having a pointed distal end and which needle protrudes or extends from the distal end of the handle, the hollow needle having an axial lumen for passing suture. The surgeon may bend exposed portions of the malleable hollow needle to a desired curvature or curved configuration to best accommodate the surgical site. The surgeon then moves the suture passer so that the distal end of the hollow needle penetrates the desired object and the suture is then passed through the needle lumen, and thereafter the hollow needle is removed from the object thereby leaving the passed suture behind.

BRIEF DESCRIPTION OF THE DRAWINGS

Other objects and advantages appear hereinafter in the following description and claims. The accompanying drawings show, for the purpose of exemplification, without limiting the scope of the invention or the appended claims, certain practical embodiments of the invention wherein:

DETAILED DESCRIPTION OF THE PREFERRED EMBODIMENTS

Figure 1:
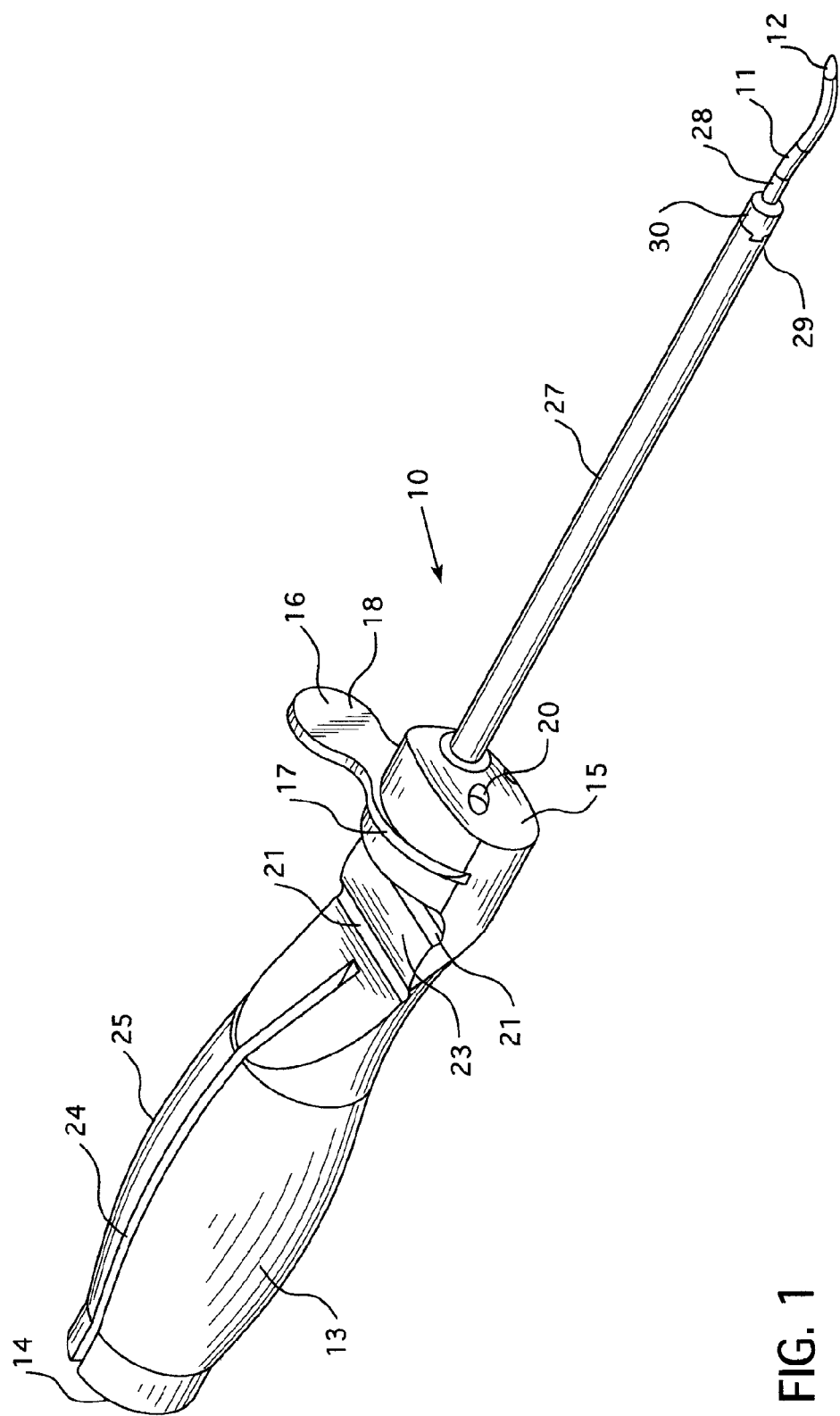
FIG. 1 is an isometric view of one embodiment of the suture passer of the present invention.
Figure 2:
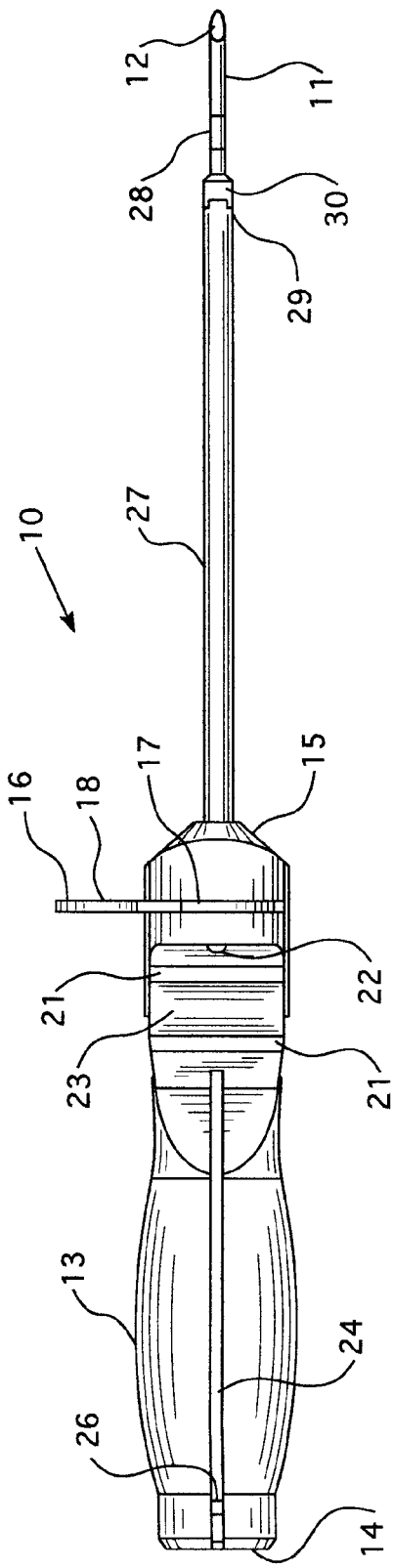
FIG. 2 is a top view of the suture passer shown in FIG. 1.
Figure 3:
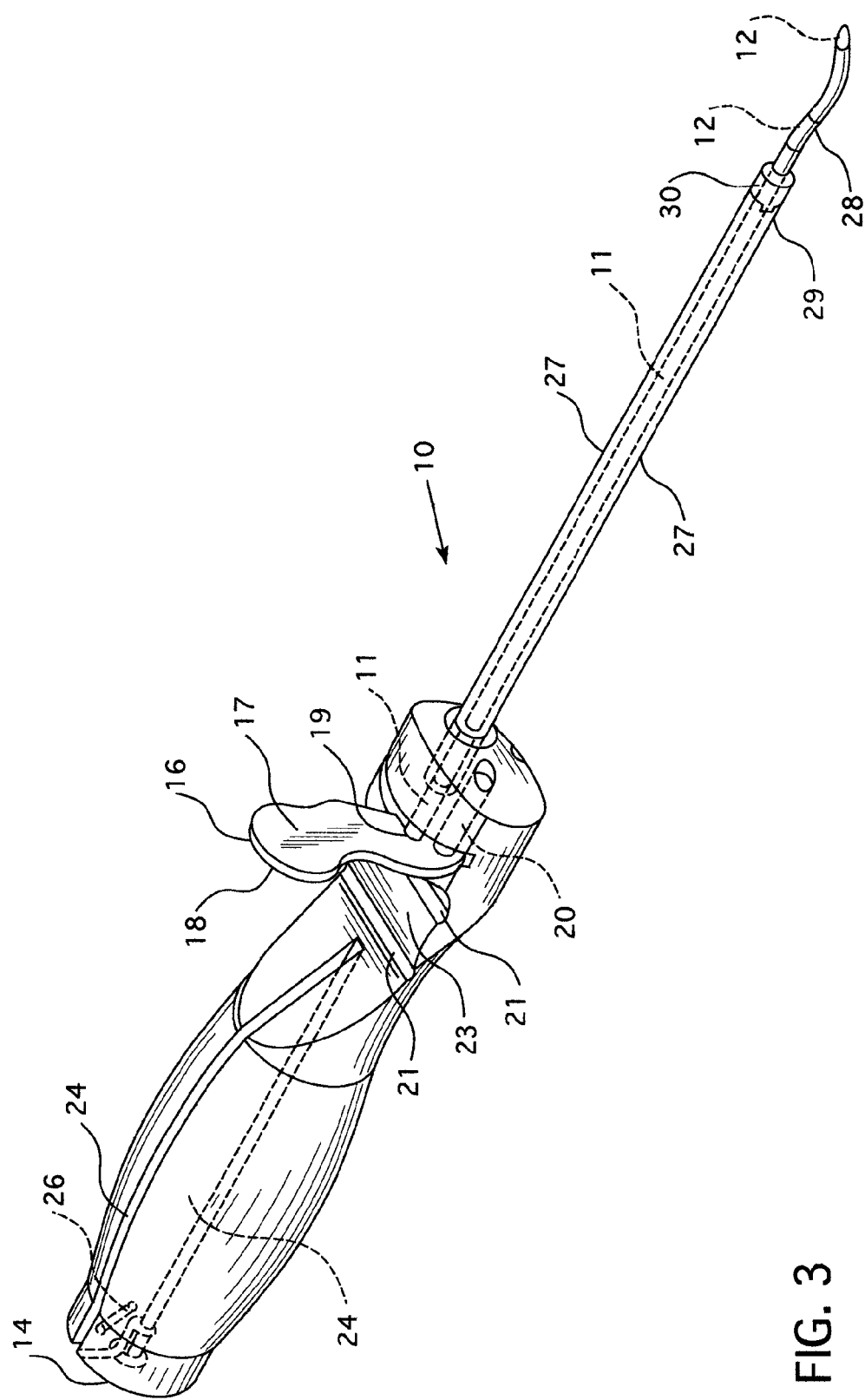
FIG. 3 is an isometric view of the suture passer shown in FIG. 1 further illustrating the needle clamp in an open condition and illustrating the internal workings of the suture passer.
Figure 4:
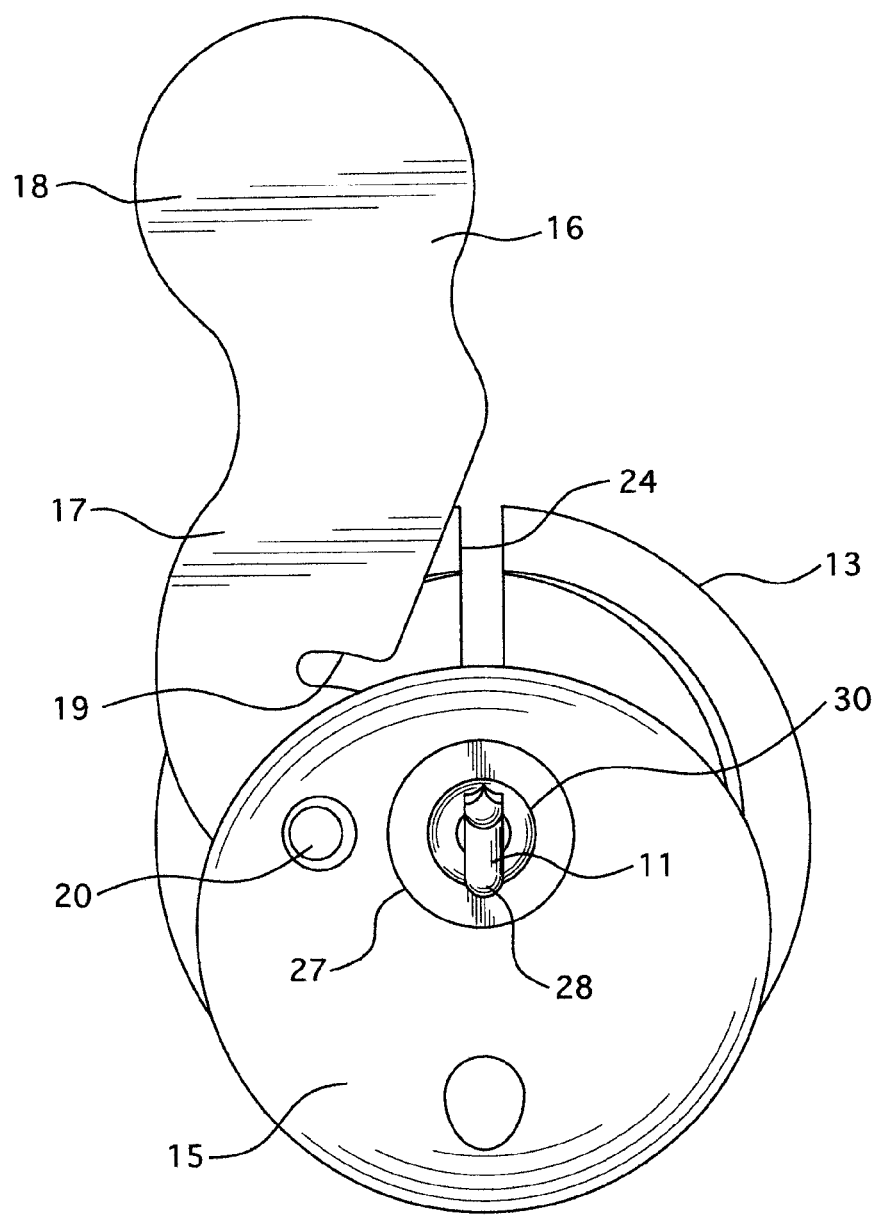
FIG. 4 is an enlarged right side end view of the suture passer shown in FIG. 3.

With reference to FIGS. 1, 2, 3 and 4, the surgical suture passer 10 of the present invention is comprised of a hollow needle 11 having an axial lumen 12 and a handle 13 having a proximal end 14 and a distal end 15. The distal end 15 is adapted to receive and retain hollow needle 11 in handle 13 by clamp 16 which is positioned in handle 13 for manipulation by a single finger of the operator for clamping and unclamping hollow needle 11 to handle 13 against axial movement. Clamp 16 in this embodiment is illustrated as a pivotal arm 17 having an outer protrusion 18 for finger engagement and manipulation and a clamping notch 19 dimensioned for engaging and binding hollow needle 11 in position. Pivotal arm 17 of clamp 16 pivots about pivot pin 20.

Hollow needle 11 is malleable whereby exposed portions of the needle 11 can be bent to a desired configuration or curvature, for example as shown in FIG. 1. Hollow needle 11 may be bent by hand or with the assistance of pliers. The more lengthy exposed needle 11 shown in the embodiment of FIG. 5 lends itself more appropriately to hand bending by the surgeon.

The handle 13 further defines a planar recessed surface 21, wherein lumen 12 of hollow needle 11 is aligned with this surface 21 via suture passage 22 whereby a suture (not shown) positioned on surface 21 may be advanced or retracted by direct finger engagement of the suture into and out of suture passage 22 and lumen 12 of hollow needle 11.

An outwardly protruding hump 23 is provided on planar recess surface 31 for enhancing the finger engagement and advancement or retraction of a suture positioned thereon into and out of the lumen 12 of hollow needle 11.

Handle 13 additionally includes a suture passageway slot 24 in a proximal end portion 25 of handle 13. Slot 24 extends rearwardly toward the proximal end 14 of handle 13 from recessed surface 21 and is substantially in alignment with the hollow needle 11 for receiving suture therein for temporary retention. Thus the handle slot 24 may be top loaded with a suture, and in order to prevent the suture from following out of slot 24, a wire spring clip 26 is provided in slot 24 which permits the suture to be forced downwardly into slot 24 past the wire spring clip 26 for retention thereunder in slot 24.

A rigid cannulated support shaft 27 is threadably secured to distal end 15 of handle 13 and receives hollow needle 11 therethrough with an outer exposed portion 28 of needle 11 keyed against rotation by keyed needle hub 30 to the outer distal end 29 of support shaft 27.

Figure 5:
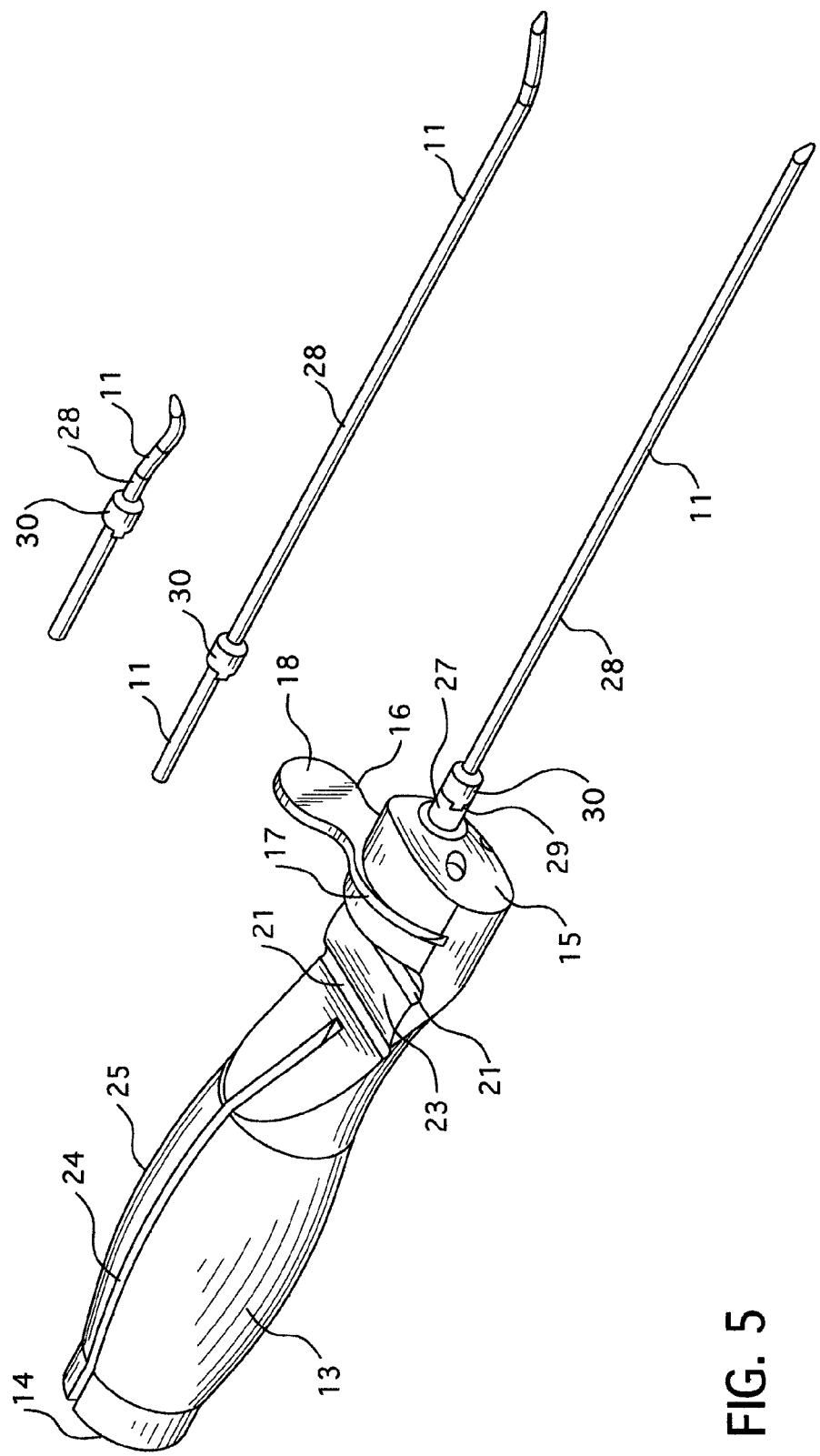
FIG. 5 is an isometric view of a second embodiment of the suture passer of the present invention shown in association with a selection of different suture needles that may be utilized with the instrument.

Referring next to the embodiment shown in FIG. 5, the suture passer 10 is in all respects identical to that of the suture passer 10 shown in the previous figures, with the exception that cannulated support shaft 27 is much shorter in length than the comparable support shaft 27 shown in the embodiment of the previous figures, thereby leaving a much larger exposed portion 28 of hollow needle 11. This permits the suture passer 10 to be adaptable by flexing or bending needle 11 to accommodate suture complexities encountered in different challenging surgical sites.

Figures 6, 6A:
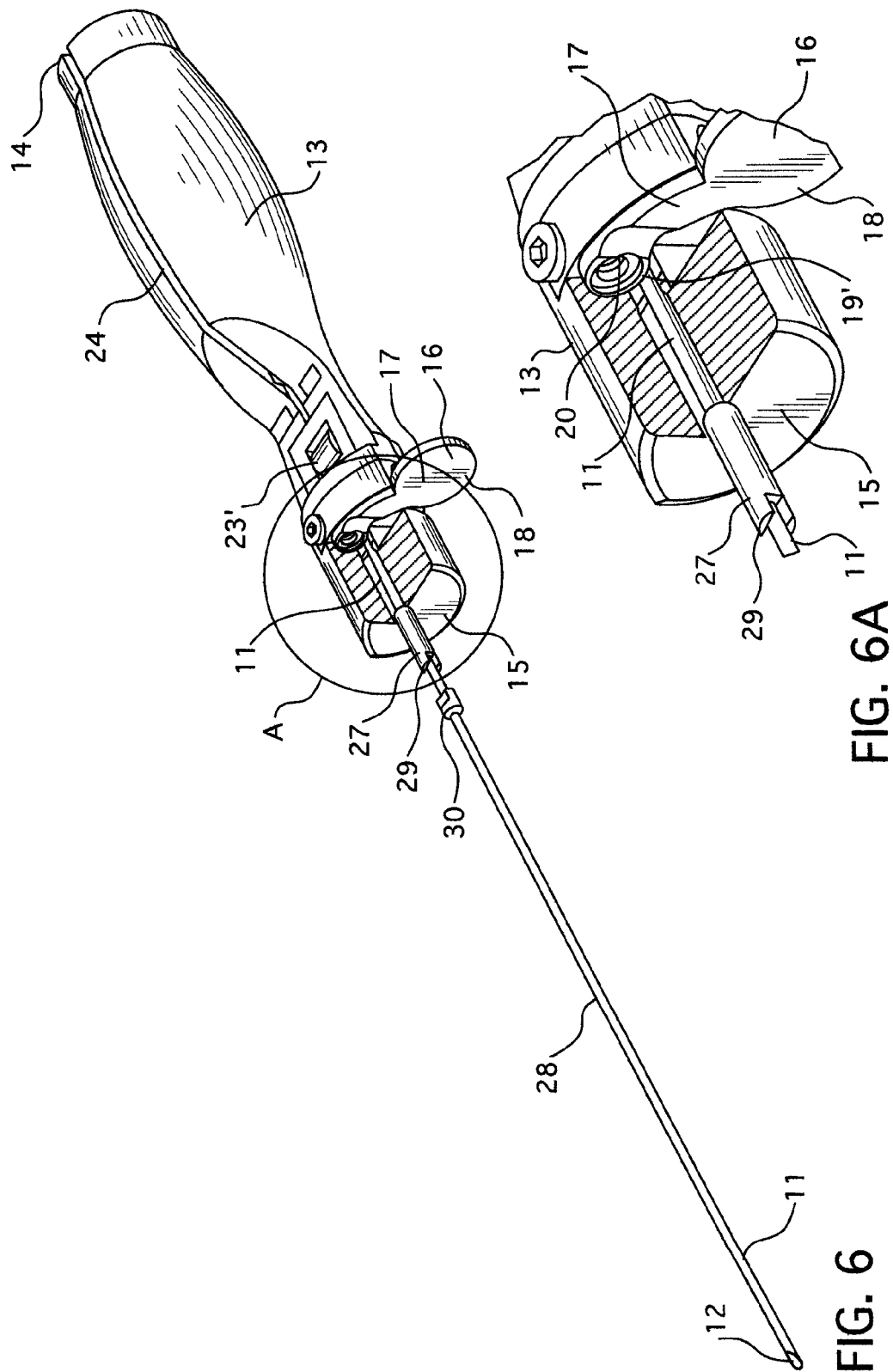
FIG. 6 is an isometric view of a third embodiment of the suture passer of the present invention with portions of the handle sectioned away for interior viewing of the needle clamp mechanism.
FIG. 6A is an enlarged detail view of the sectioned portion of FIG. 6.

Turning next to the embodiment illustrated in FIGS. 6 and 6A, the surgical suture passer 10 is identical in structure and method of operation of the previous embodiments with the exception that hump 23 is replaced with roller 23' and clamp 16 is provided in the form of a lever arm 17 as in the previous embodiments, except needle engagement slot 19 is substituted with cam surface 19' which engages and binds needle 11 against axial movement relative to handle 13 when clamp lever arm 17 is in the closed position as illustrated in FIGS. 6 and 6A.

We claim:

1. A surgical suture passer comprising:
    a hollow needle having an axial lumen;
    a handle having a proximal end and a distal end, said distal end adapted to receive and retain said hollow needle, said handle defining a planar recessed surface, said lumen in said hollow needle being aligned with said surface when said needle is retained by said handle whereby a suture positioned on said surface may be advanced or retracted by direct finger engagement of said suture into or out of said lumen; and
    a clamp in said handle positioned and manipulatable by a single finger for clamping and unclamping said hollow needle to said handle against axial movement;
    characterized in that said clamp is a pivotal arm that pivots in a direction transverse to said hollow needle about a pivot point on said handle which has a pivot axis in parallel alignment with said hollow needle and is dimensioned whereby an edge of said pivotal arm engages a side surface of said hollow needle thereby binding said hollow needle in position by using a single finger.

2. The surgical suture passer of claim 1, wherein said pivotal arm has a notch dimensioned for engaging and binding said hollow needle in position.

3. The surgical suture passer of claim 1, wherein said hollow needle is malleable whereby it may be bent to a desired curvature.

4. The surgical suture passer of claim 1, wherein said surface includes an outwardly protruding hump for enhancing the finger engagement and advancement or retraction of a suture positioned thereon into or out of said lumen.

5. The surgical suture passer of claim 4, wherein said hump is comprised of a roller.

6. The surgical suture passer of claim 1, wherein said handle includes a suture passageway slot in a proximal end portion of said handle, said slot extending rearwardly toward said proximal end from said recessed surface and substantially in alignment with said hollow needle for receiving suture therein for temporary retention.

7. The surgical suture passer of claim 6, including a spring clip in said slot which permits suture to be forced downwardly in said slot past said clip for retention under said clip.

8. The surgical suture passer of claim 1, including a rigid cannulated support shaft secured to the distal end of said handle and receiving said hollow needle therethrough with an outer exposed portion of said needle keyed against rotation to the outer distal end of said shaft.

9. The surgical suture passer of claim 8, wherein said pivotal arm has a notch dimensioned for engaging and binding said hollow needle in position.

10. The surgical suture passer of claim 8, wherein said hollow needle is malleable whereby an exposed portion thereof may be bent to a desired curvature.

11. The surgical suture passer of claim 8, wherein said surface includes an outwardly protruding hump for enhancing the finger engagement and advancement or retraction of a suture positioned thereon into or out of said lumen.

12. The surgical suture passer of claim 11, wherein said hump is comprised of a roller.

13. The surgical suture passer of claim 8, wherein said handle includes a suture passageway slot in a proximal end portion of said handle, said slot extending rearwardly toward said proximal end from said recessed surface and substantially in alignment with said hollow needle for receiving suture therein for temporary retention.

14. The surgical suture passer of claim 13, including a spring clip in said slot which permits suture to be forced downwardly in said slot past said clip for retention under said clip.

* * * * *